US009791448B2

(12) United States Patent
Linley et al.

(10) Patent No.: US 9,791,448 B2
(45) Date of Patent: Oct. 17, 2017

(54) BREAST CANCER ASSAY

(71) Applicant: THE NOTTINGHAM TRENT UNIVERSITY, Nottingham, Nottinghamshire (GB)

(72) Inventors: Adam Linley, Nottingham (GB); Stephanie Mcardle, Nottingham (GB); Chungui Lu, Nottingham (GB); Robert Rees, Nottingham (GB); Stephen Yan Tat Chan, Nottingham (GB); Tarek Mohamed Ahmed Abdel-Fateh, Nottingham (GB)

(73) Assignee: THE NOTTINGHAM TRENT UNIVERSITY, Nottingham (GB)

( * ) Notice: Subject to any disclaimer, the term of this patent is extended or adjusted under 35 U.S.C. 154(b) by 0 days.

(21) Appl. No.: 14/389,108

(22) PCT Filed: Mar. 27, 2013

(86) PCT No.: PCT/GB2013/050794
§ 371 (c)(1),
(2) Date: Sep. 29, 2014

(87) PCT Pub. No.: WO2013/144616
PCT Pub. Date: Oct. 3, 2013

(65) Prior Publication Data
US 2015/0118248 A1    Apr. 30, 2015

(30) Foreign Application Priority Data

Mar. 27, 2012 (GB) .................................. 1205361.7

(51) Int. Cl.
| | | |
|---|---|---|
| G01N 33/53 | (2006.01) | |
| G01N 33/574 | (2006.01) | |
| A61K 31/704 | (2006.01) | |

(52) U.S. Cl.
CPC ..... *G01N 33/57415* (2013.01); *A61K 31/704* (2013.01); *G01N 2333/914* (2013.01); *G01N 2800/52* (2013.01)

(58) Field of Classification Search
None
See application file for complete search history.

(56) References Cited

U.S. PATENT DOCUMENTS

2010/0255471 A1* 10/2010 Clarke ................. C12Q 1/6886
                                                                    435/6.14
2011/0217297 A1*  9/2011 Kao ................... G01N 33/57415
                                                                    424/133.1

FOREIGN PATENT DOCUMENTS

| WO | 9953061 A2 | 10/1999 |
| WO | 2005055601 A2 | 1/2005 |
| WO | 2005039634 A1 | 5/2005 |
| WO | 2011109637 A1 | 9/2011 |
| WO | 2011130495 A1 | 10/2011 |

OTHER PUBLICATIONS

Abdel-Fatah et al.; "Hage (DDX43) Protein Expression is a Powerful Independent Biomarker of Poor Clinical Outcome of Breast Cancer (BC) and Could be a Potential Therapeutic Target for ER Negative BC" J. Pathol.; vol. 228, No. 1; Aug. 24, 2012; p. S11.
Chan et al.; "HAGE (DDX43) protein expression as an independent biomarker of poor clinical outcome of breast cancer (BC) and potential as a therapeutic target for ER-negative BC"; J. Clin. Oncol. 30, 2012 (suppl; abstr. 1013) as Published on Meeting Library (http://meetinglibrary.asco.org), downloaded on Nov. 12, 2015; 2012; pp. 1-2.
Gianni et al.; "Efficacy and safety of neoadjuvant pertuzumab and trastuzumab in women with locally advanced, inflammatory, or early HER2-positive breast cancer (NeoSphere): a randomised multicentre, open-label, phase 2 trial"; The Lancet Oncology; vol. 13; Jan. 2012; pp. 25-32.
Mathieu et al., "HAGE, a cancer/testis antigen expressed at the protein level in a variety of cancers"; Cancer Immunity; vol. 10; Jan. 2010; pp. 1-8.
International Search Report of the International Searching Authority for International Patent Application No. PCT/GB2013/050794; International Filing Date: Mar. 27, 2013; Date of Mailing: Aug. 19, 2013; 4 Pages.
Written Opinion of the International Searching Authority for International Patent Application No. PCT/GB2013/050794; International Filing Date: Mar. 27, 2013; Date of Mailing: Aug. 19, 2013; 6 Pages.

\* cited by examiner

*Primary Examiner* — Michael Pak
(74) *Attorney, Agent, or Firm* — Cantor Colburn LLP

(57) ABSTRACT

The application describes a method of screening for breast cancer by testing fro the amount of HAGE (Helicase antigen) in a sample of breast tissue. Methods of prognosis of samples of breast cancer tumours are also provided. HAGE+ ER− (estrogen receptor-) cancers are indicated as being amenable to chemotherapy. Methods of treating breast cancers with HAGE-specific CTA antigen or HAGE-specific antibodies are also provided.

6 Claims, 6 Drawing Sheets

BREAST CANCER ASSAY

CROSS-REFERENCE TO RELATED APPLICATIONS

Figure 1:
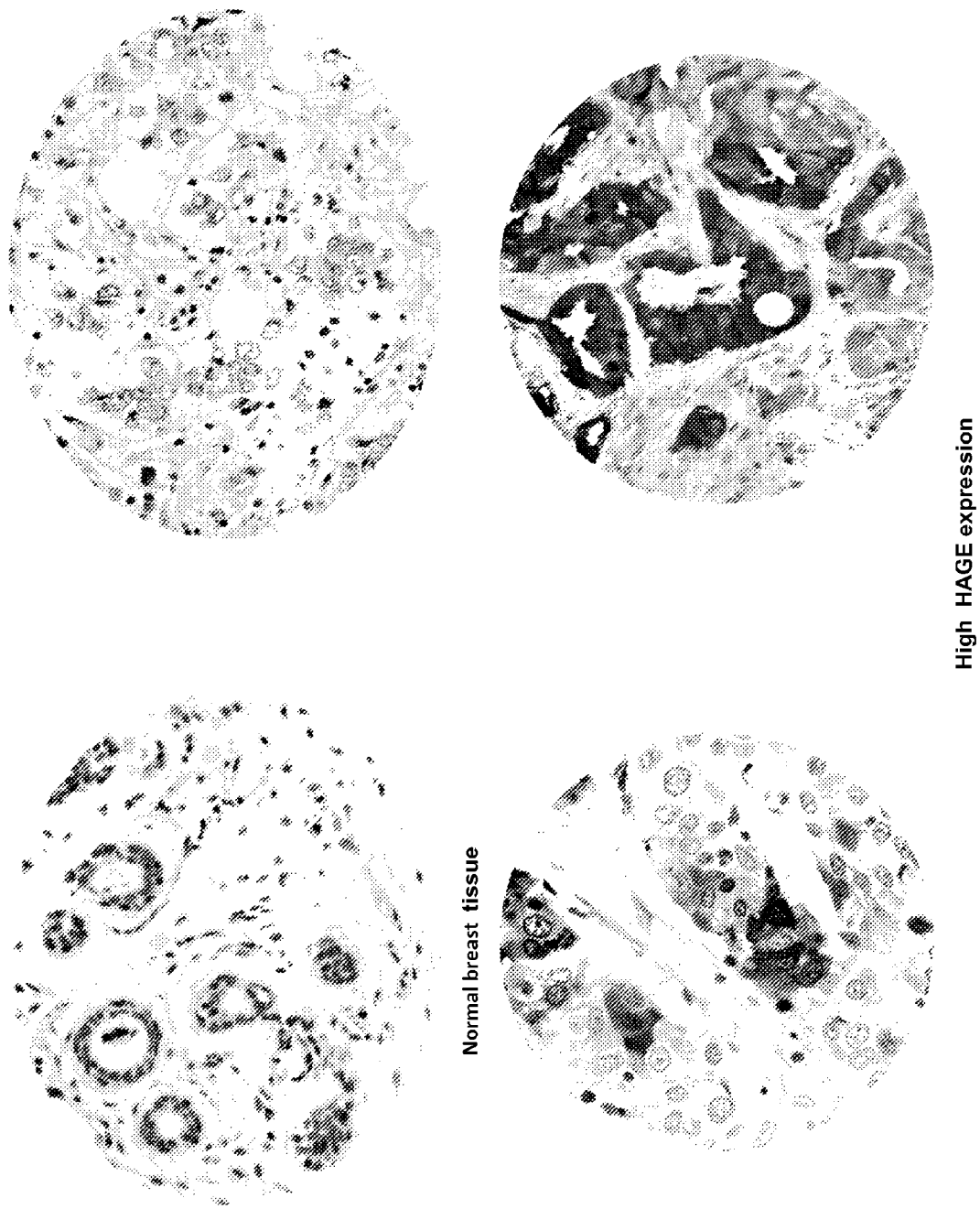

This Application is a U.S. National Stage Application of PCT/GB2013/050794 filed Mar. 27, 2013 which is incorporated by reference in its entirety.

The invention relates to a method of identifying aggressive breast cancer tumours by considering the HAGE expression in the tumours.

Breast cancer (BC) remains the most common cancer and is the leading cause of cancer deaths in women. In spite of improved outcome by earlier detection, and recent advances in adjuvant therapy (AT), many patients still develop recurrence[1-3]. Nowadays there is a shift in cancer therapy from 'one size fits all' to a personalized and tailored treatment for individual patients to increase efficiency and avoid unnecessary toxicity. There is an urgent need to identify biomarkers that can help in risk assessments and could act as novel therapeutic targets[4-5]. Immunotherapy which targets tumour specific antigen (TSA) can be used to control tumour growth and prevent metastases[6]. Identification of TSA that act as target antigens for cytotoxic and helper T cells, is a prerequisite to establishing an effective immunotherapy strategy, but unfortunately there is a lack of such TSA in BC.

The Helicase Antigen known as HAGE, and DDX43, was first identified using representational difference analysis in a sarcoma cell line[7] and was shown to be expressed in many tumour samples but not in any normal tissues tested[6-8] except testis. The inventors have previously reported that HAGE protein was found to be both immunogenic and required for cancer cells proliferation. These properties would suggest that HAGE could be explored as a target for immunotherapy and could also be utilized as a biomarker in BC.

The invention provides a method for screening breast cancer which comprises testing a sample of breast tissue from a subject for the level of HAGE expression in the sample.

The Applicant has shown for the first time that HAGE may be over-expressed in breast tissue and that over-expression is associated with a more aggressive breast cancer. Moreover, it is possible to articulate a prognosis for the cancer and identify patients who should be clinically treated in particular ways based on the level of HAGE expression in the tumours.

The invention also provides a method of testing breast cancer from a subject for a likely prognosis of the breast cancer comprising testing a sample of a breast cancer (BC) from the subject for level of HAGE expression In the method of the invention a HAGE+ result indicates an increased probability that the cancer is aggressive and has a decreased probability for a likely long term survival of the subject.

HAGE+ may be determined by staining tissue samples with labelled HAGE-specific antibodies. The presence of strong cytoplasmic and/or nuclear staining in >10% of the malignant cells indicates HAGE+. The normal breast tissues showed negative HAGE expression (HAGE−) throughout.

HAGE overexpression (HAGE+) was observed in 10% of BC and was significantly associated with aggressive clinicopathological features including: ER−, high grade, high proliferation index, triple receptor negative (TNT) phenotypes, over-expression of HER2 and p53 mutation. HAGE has been found to be significant in TNBC (triple negative breast cancer) patients who lack significant expression of ER, progesterone receptor (PR) and human epidermal growth factor 2 (HER2).

HAGE+ patients have increased risk of deaths in the long term, for example 10 years. In high risk BC patients who did not received any adjuvant therapy, HAGE+ expression showed an adverse outcome with a 2-4 fold increase in the risk of death, recurrence and metastases compared to HAGE−; ps<0.0001. The poor clinical outcome of HAGE+ was further confirmed in low risk BrCa patients (NPI<3.4), treated with surgery followed by radiotherapy only. Notably, the 10-year survival probability of low risk BrCa patients with HAGE− expression was 94% which is indistinguishable from that of age-matched females without BrCa. Using a multivariate Cox regression model including ER status, grade, size and tumour stage, HAGE expression was confirmed as a powerful independent prognostic factor (p<0.0001)

The methods of the invention may also involve the testing of a sample of the breast cancer or breast tissue for estrogen receptors (ER), progesterone receptors (PR) and/or human epidermal growth factor 2 (HER2). This is already carried out on a regular basis in hospitals. ER is often used to assist in determining possible therapies for the cancer.

High risk ER+ patients received endocrine therapy, HAGE+ patients were observed to have had 3-fold higher risk of death, recurrence and distant metastases at 10 years than patients with HAGE-expression. Similarly, HAGE+ high risk (NPI>3.4)/ER negative patients who did not received any chemotherapy had 2-4 fold increase in the risk of death, recurrence and DM compared to those with HAGE− expression.

While, adjuvant CT either CMF or ATC had a positive impact on HAGE+, high risk ER− BC as HAGE+ had a similar risk of death, recurrence and distant metastases to HAGE− expression. This suggests that HAGE+ ER− patients should benefit from chemotherapy. Hence the method also includes the step of treating a HAGE+ patient, such as HAGE ER− or HAGE+ ER− RP− HER2−, with chemotherapy such as anthracycline chemotherapy (ACT).

The invention also provides a breast chemotherapeutic agent, such as an anthracycline chemotherapeutic agent for use in the treatment of HAGE+, such as HAGE+ ER− or HAGE+ ER− PR− HER2−, breast cancers.

The amount of HAGE and optionally ER maybe determined immunologically using HAGE (or ER or PR or HER2)-specific antibodies or fragments thereof.

ELISA, for example, uses antibodies to detect specific antigens. One or more of the antibodies used in the assay may be labelled with an enzyme capable of converting a substrate into a detectable analyte. Such enzymes include horseradish peroxidase, alkaline phosphatase and other enzymes known in the art. Alternatively, other detectable tags or labels may be used instead of, or together with, the enzymes. These include radioisotopes, a wide range of coloured and fluorescent labels known in the art, including fluorescein, Alexafluor, Oregon Green, BODIPY, rhodamine red, Cascade Blue, Marina Blue, Pacific Blue, Cascade Yellow, gold; and conjugates such as biotin (available from, for example, Invitrogen Ltd, United Kingdom). Dye sols, metallic sols, chemiluminescent labels or coloured latex may also be used. One or more of these labels may be used in the ELISA assays according to the various inventions described herein, or alternatively in the other assays, labelled antibodies or kits described herein.

The construction of ELISA-type assays is itself well known in the art. For example, a "binding antibody" specific for the HAGE is immobilised on a substrate. The "binding antibody" may be immobilised onto the substrate by methods which are well known in the art. HAGE in the sample are bound by the "binding antibody" which binds the HAGE to the substrate via the "binding antibody".

Unbound immunoglobulins may be washed away.

The labelled antibodies may also be used to stain the tissue so that the stained cells can be counted, for example under a microscope.

The antibodies may be polyclonal or monoclonal and may be (Fab)2 or Fab antibodies. They are generally known in the art but may be made by methods generally known in the art.

HAGE or ER expression may also be determined using quantitative PCR to determine the level of HAGE (or ER or PR or HER2) expression in the sample and quantitative PCR is known per se in the art.

HAGE is an antigenic marker. It may therefore be used to target therapeutic agents to treat the breast cancer, for example by targeting a HAGE CTA antigen.

Anti-HAGE antibodies are generally known in the art, see for example Mathieu et al Cancer Immunity (2010) 10, 2-9. Both polyclonal and monoclonal antibodies specific for HAGE are commercially available from a number of commercial sources including Abgent and Abcam.

A range of different antibody-based therapies are known per se. For example, Bevacizumab (for colorectal cancer), Cetuximab (colorectal, head an neck cancer), Gemtuzumab (leukaemia), Ipilimuman (melanoma) and herceptin (breast cancer via targeting Erb B2). Modes of action generally known include blocking receptors and introducing a cytotoxin, such as yttrium 90 or indium 111, ADEPT (Antibody Directed Prodrug Therapy) and using immunoliposomes to introduce cytotoxins (Breast. Dis (2000), 11, 113-124). Similar strategies may be adopted to produce anti-HAGE therapies.

HAGE-specific vaccines may also be used to prevent or treat breast cancer, Mathieu et al (2010, supra) discuss the identification and production of HAGE-specific immunogenic peptides.

Anti-HAGE antibodies and HAGE-specific vaccines for use in the treatment of breast cancers are also provided.

The antibodies and vaccines may be used in conjunction with a methyltransferase inhibitor, such as 5-aza-2'-deoxycytidine. Such drugs induce HAGE expression.

The invention therefore also provides a method of treating breast cancer comprising treating the patient with a HAGE-specific antibody, optionally attached to a cytotoxic compound.

Assay kits comprising optionally labelled anti-HAGE and one or more or all of anti-ER, anti-PR and/or anti-HER2 antibodies, or fragments thereof, as optionally described above, are provided.

The invention will now be described by way of example only with reference to the following figures:

FIG. 1: Microphotographs of HAGE1 expression in normal and breast cancer tissue (magnification×200).

Figure 2:
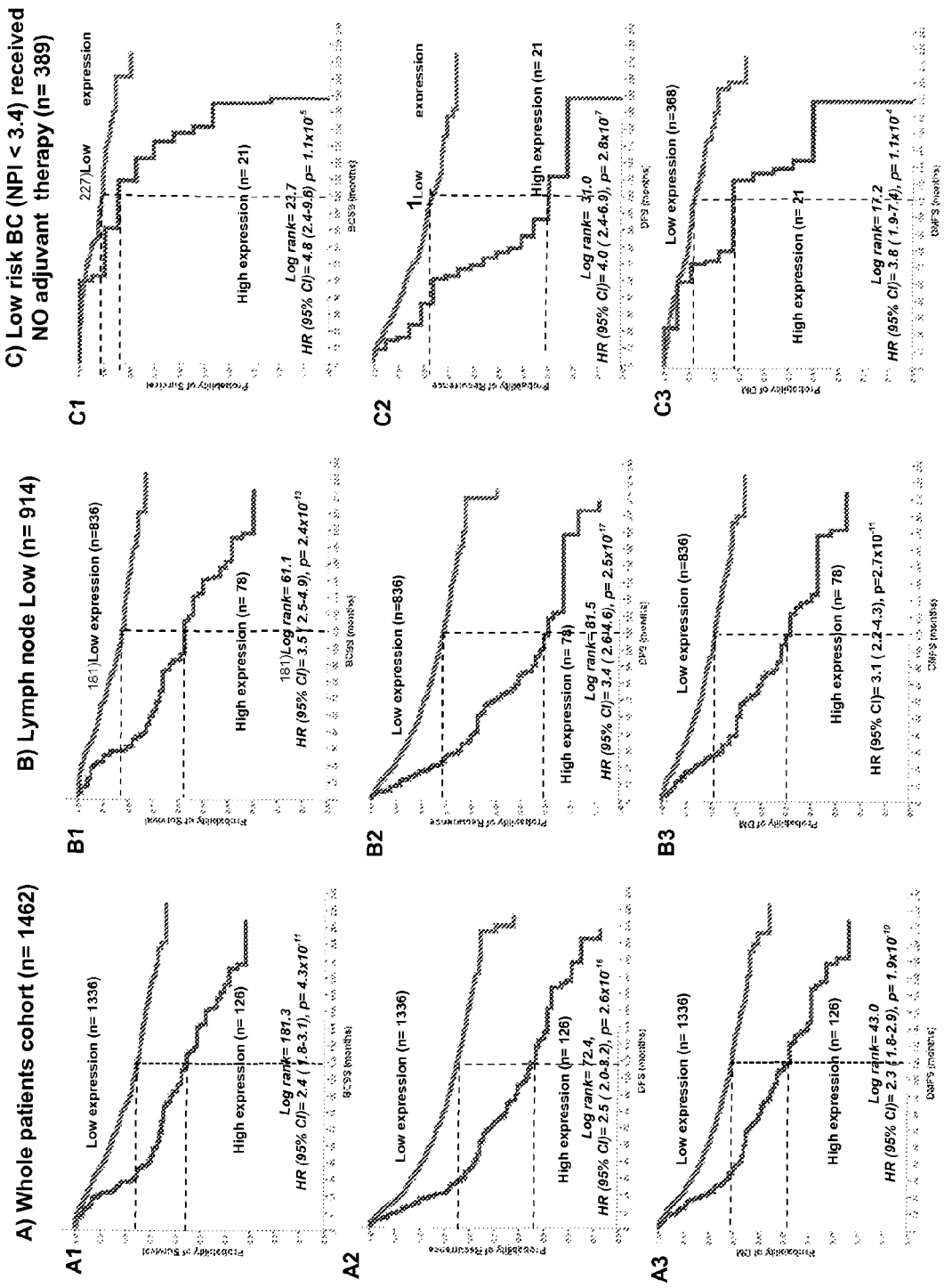

FIG. 2: Kaplan Meier curves showing breast cancer specific survival (BCSS), disease free survival (DFS) and distant metastasis free survival (DMFS) in the whole cohort (A), lymph node negative sub-group (B) and in low risk BC (NPI<3.4) received no adjuvant therapy (C). See text for details.

Figure 3:
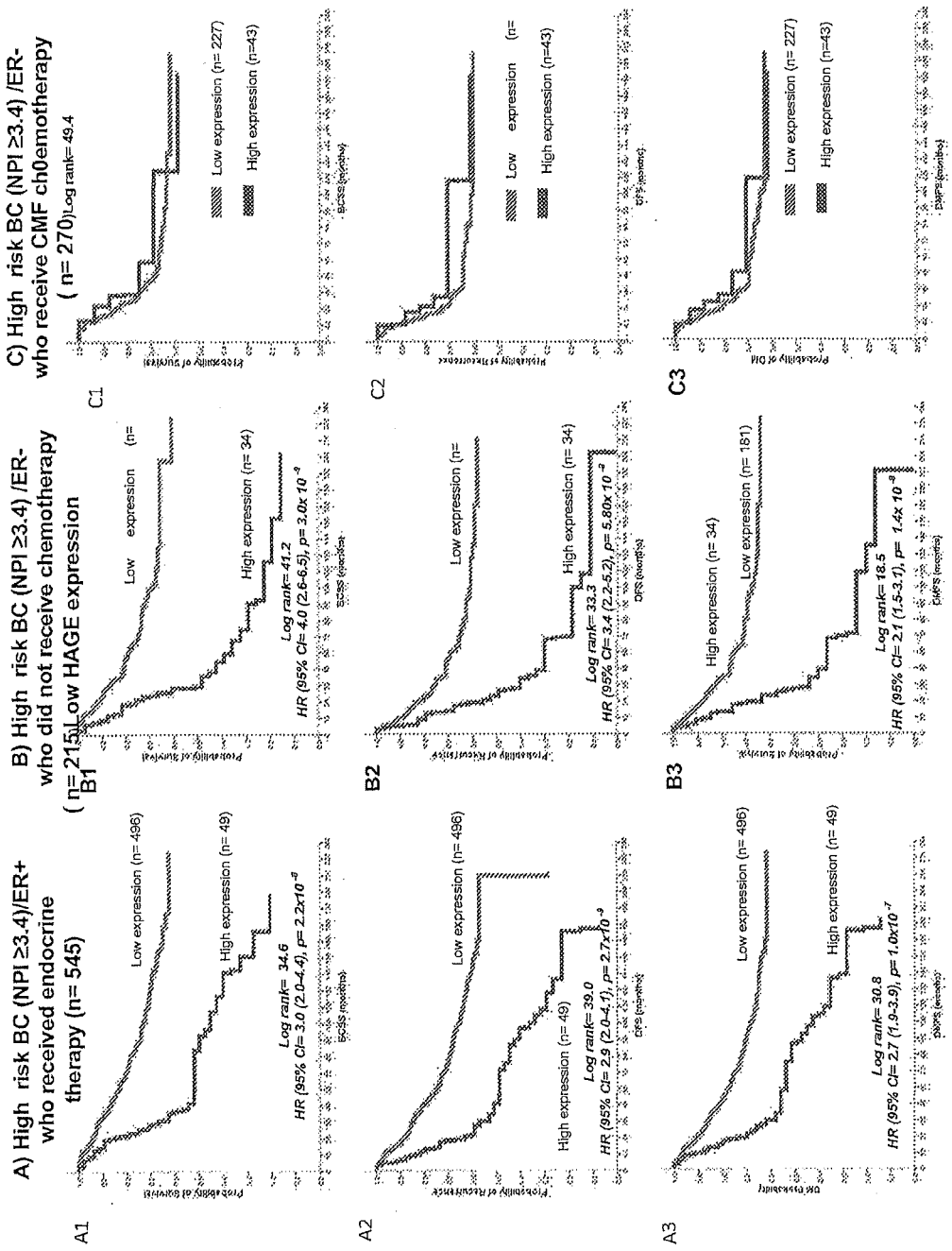

FIG. 3: Kaplan Meier curves showing breast cancer specific survival (BCSS), disease free survival (DFS) and distant metastasis free survival (DMFS) high risk BC (NPI≥3.4) ER+ who received endocrine therapy (A), ER negative/high risk BC (NPI≥3.4) who received no CMF chemotherapy because they diagnosed and treated before 1989 (B) and ER negative/high risk BC (NPI≥3.4) who did received CMF chemotherapy because they diagnosed and treated after 1989 (C). See text for details.

Figure 4:
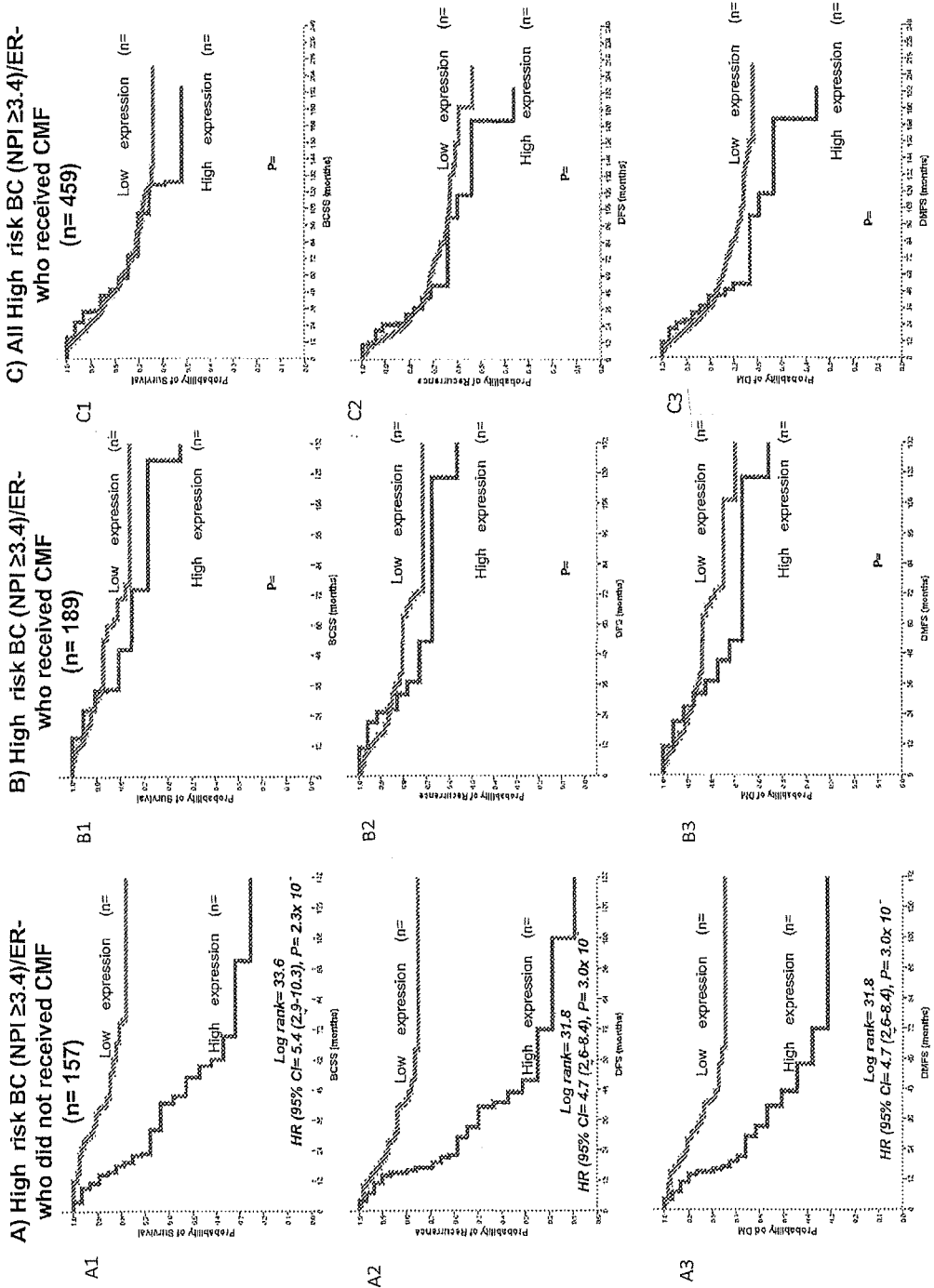

FIG. 4: ER negative independent validation cohort. Kaplan Meier curves showing breast cancer specific survival (BCSS), disease free survival (DFS) and distant metastasis free survival (DMFS) in the ER negative/high risk BC (NPI≥3.4) who received no chemotherapy (A), ER negative/high risk BC (NPI≥3.4) who did received anthracycline chemotherapy (B) and All ER negative/high risk BC (NPI≥3.4) patients (in both study and validation sets) who did received adjuvant chemotherapy (C). See text for details.

Figure 5:
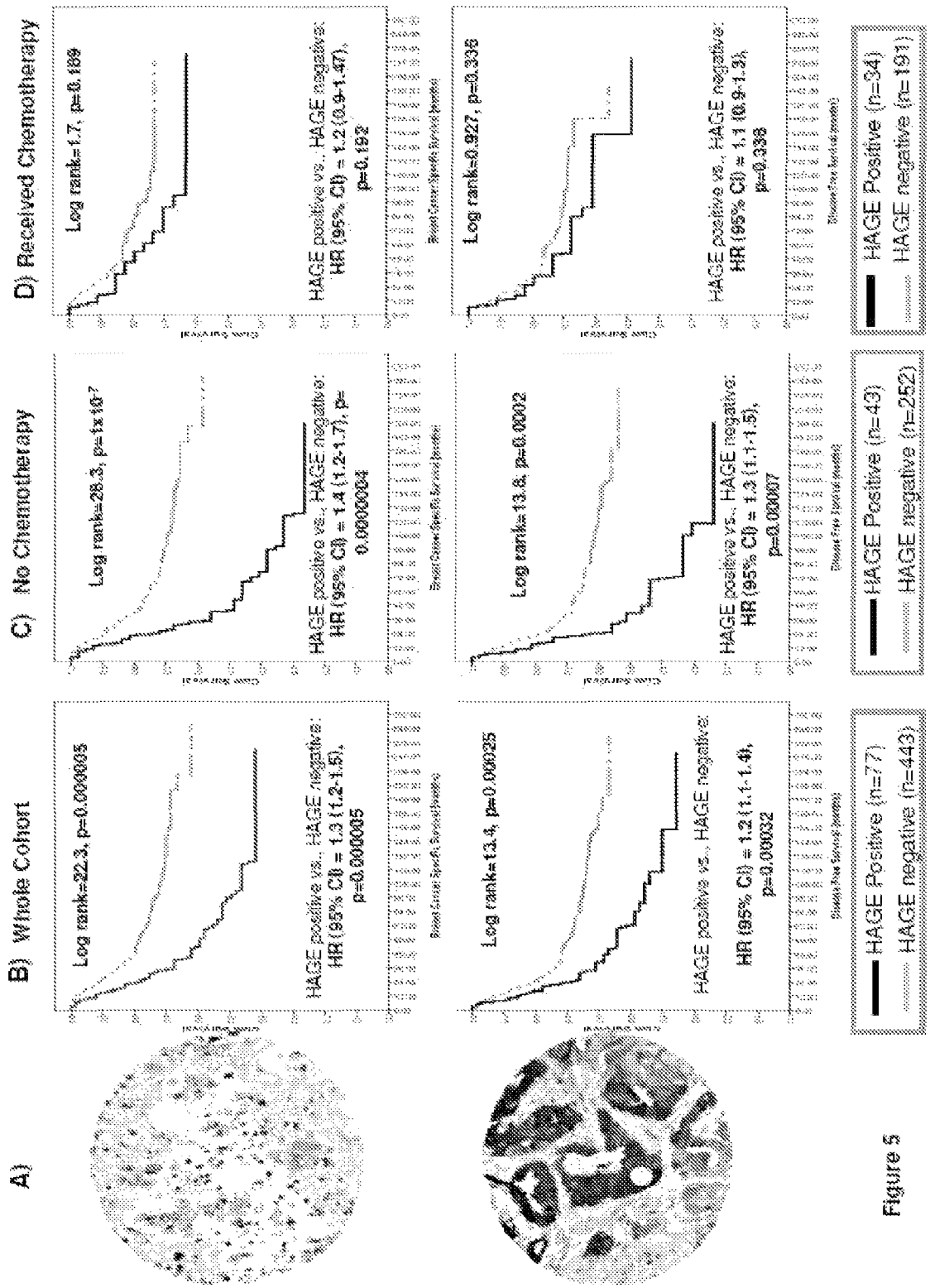

FIG. 5: Clinical outcome of HAGE expression of primary operable TNBC in different adjuvant settings. Panel A, HAGE staining of BC cells; Panel B, Whole cohort Kaplan-Meier plot; Panel C, No chemotherapy Kaplan-Meier plot; Panel D, Received chemotherapy Kaplan-Meier plot.

Figure 6:
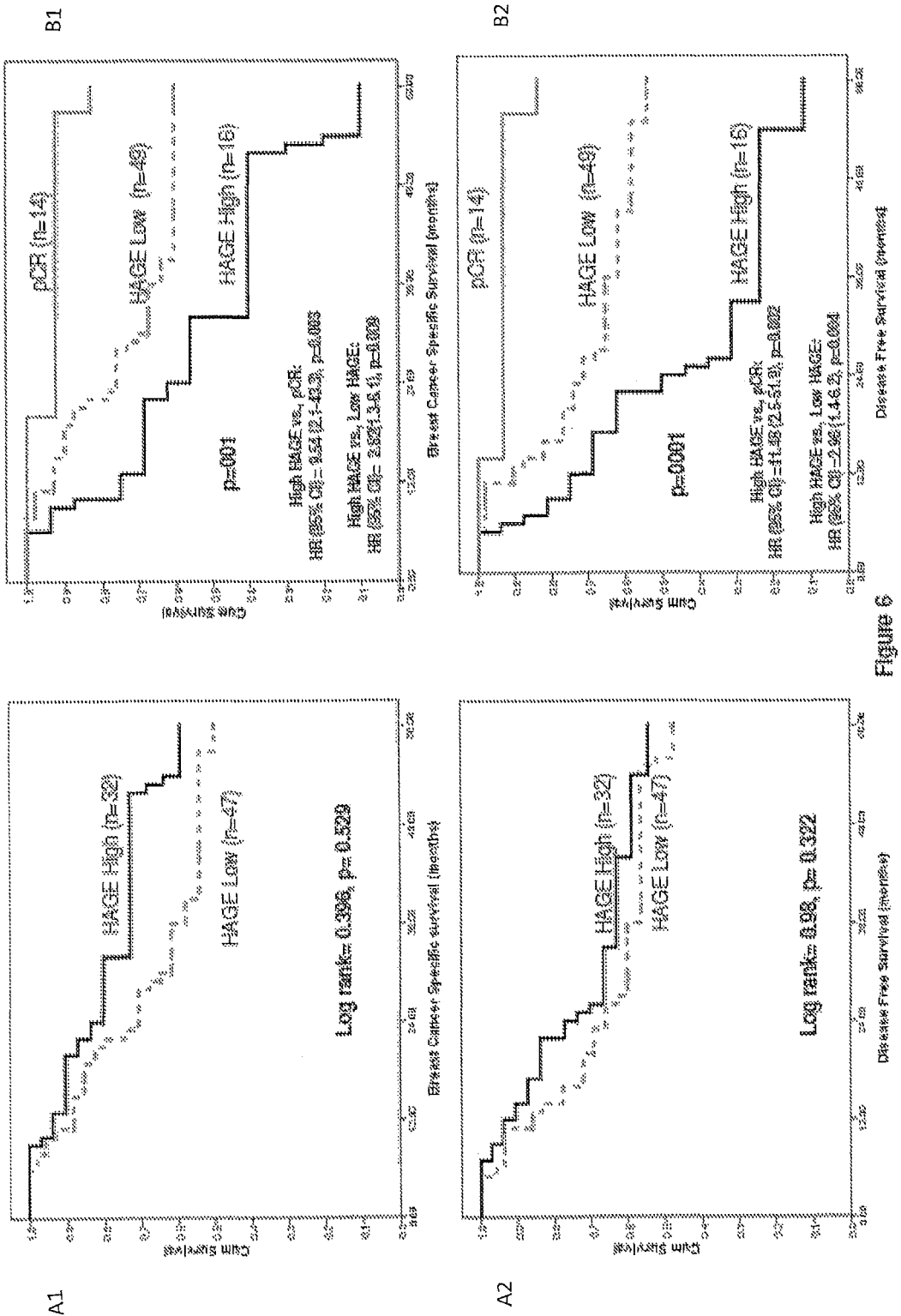

FIG. 6: Clinical outcome of primary locally advancer triple negative (PLA-TNBC) according to HAGE expression in pre-neo-adjuvant (Graphs A1 an A2) and post-neo-adjuvant (Graphs B1 and B2) chemotherapy samples.

PATIENTS AND METHODS

Study Patients

This is a retrospective study in a consecutive series of 1650 patients with primary invasive BCs who were diagnosed and treated in a single centre with the same treatment protocol from 1989 to 1999—the Nottingham Tenovus Primary BC series. This is a well-characterized series of patients under the age of 71 years (median, 55 years) with long-term follow-up (range=1-240 months, median=130 months). Detailed Patient demographics and clinico-pathological characteristics were routinely assessed (Table S1)[10]. Patients received standard surgery (mastectomy or wide local excision) with radiotherapy. Based on well characterized prognostic and predictive factors including; Nottingham prognostic index (NPI), oestrogen receptor-α (ER) status, and menopausal status. Patients with NPI scores of <3.4 (low risk) did not receive AT. Patients with ER positive (ER+) tumours and NPI scores of >3.4 (high risk) were given endocrine therapy (ET). In pre-menopausal patients and ER− postmenopausal patients with NPI scores of ≥3.4 (high risk) Cyclophosphamide, Methotrexate, and 5-Flourouracil (classical CMF) chemotherapy (CT) was given; and patients with ER+ tumour were also offered ET. Exploratory subgroup analysis of HAGE expression was also performed in lymph node (LN) negative vs. LN positive cases, high risk patients (NPI>3.4) who received CT vs. CT-naïve cases and in ER+ high risk patients who received ET vs. ET-naïve cases.

Validation Cohorts

In order to validate the value of HAGE protein expression as a biomarker in the context of modern combination cytotoxic chemotherapy, we also analysed its expression in an independent series of 300 ER− BC patients who did not received any CT treated before 1986. 396 ER− BC diagnosed and managed at the same institution (Nottingham University Hospitals) between 1999 and 2007. Patients were primarily treated with surgery followed by radiotherapy and anthracycline combination chemotherapy. Comprehensive follow-up data was available for 389 patients, ranging from 2 to 167 months (median=89 months, mean=86 months). The characteristics of this cohort are summarised in Table S2.

Survival Data

Survival data including survival time, disease-free survival (DFS), and development of loco-regional and distant metastases (DM) were maintained on a prospective basis. DFS was defined as the number of months from diagnosis to the occurrence of local recurrence, local LN relapse or DM relapse. BC specific survival (BCSS) was defined as the number of months from diagnosis to the occurrence of BC related-death. DM-free survival was defined as the number of months from diagnosis to the occurrence of DM relapse. Survival was censored if the patient was still alive, lost to follow-up, or died from other causes.

The Reporting Recommendations for Tumor Marker Prognostic Studies (REMARK) criteria[12] were followed throughout this study. This work was approved by Nottingham Research Ethics Committee.

Tissue Microarrays (TMAs) and Immunohistochemistry (IHC)

Tumours were arrayed in tissue microarrays (TMAs) constructed with 2 replicate 0.6 mm cores from the centre and periphery of the tumours for each patient. The TMAs were immunohistochemically profiled for HAGE and other biological antibodies (Online Table S3) as previously described[13-14]. Immunohistochemical staining was performed using NOVOLINK Detection kit according to the manufacturer instructions (Leica Microsystems). TMA sections were incubated overnight at room temperature with 1/175 Anti-HAGE rabbit polyclonal mono-specific antibody (custom made) 6. In addition we validated our results using a commercially available antibody that was developed and validated by Human Protein Atlas (HPA) project (anti DDX43; HPA031381, Sigma-Adrich). Pre-treatment of TMAs section was performed with citrate buffer (pH 6.0) antigen for 20 minutes. To validate the use of TMAs for immuno-phenotyping, full-face sections of 40 cases were stained and the protein expression levels of the different antibodies were compared. The concordance between TMAs and full-face sections was excellent (kappa=0.8). Positive and negative (omission of the primary antibody and IgG-matched serum) controls were included in each run.

Evaluation of Immunohistochemical Staining

The tumour cores were evaluated by three pathologists of co-authors blinded to the clinico-pathological characteristics of patients in two different settings. There was excellent intra and inter-observer agreements (k>0.8; Cohen's κ and multi-rater κ tests, respectively). Whole field inspection of the core was scored and intensities of both nuclear and cytoplasmic staining were grouped as follows: 0=no staining, 1=weak staining, 2=moderate staining, 3=strong staining. The percentage of each category was estimated. High HAGE (HAGE+) expression was defined as the presence of strong cytoplasmic and/or nuclear staining in >10% of malignant cells. Not all cores within the TMA were suitable for MC analysis as some cores were missing or lacked tumour.

Statistical Analysis

Data analysis was performed using SPSS (SPSS, version 17 Chicago, Ill.). Where appropriate, Pearson's Chi-square, Fisher's exact, Student's t and ANOVAs one way tests were used. Cumulative survival probabilities were estimated using the Kaplan-Meier method and differences between survival rates were tested for significance using the log-rank test. Multivariate analysis for survival was performed using the Cox hazard model. The proportional hazards assumption was tested using standard log-log plots. Hazard ratios (HR) and 95% confidence intervals (95% CI) were estimated for each variable. All tests were two-sided with a 95% CI and a $p$ value of <0.05 considered significant. For multiple comparisons, $p$ values were adjusted according to Holm-Bonferroni correction method 18.

Sample Size and Power Analysis

Power of study, sample size and effect size were determined by using PASS program (NCSS, version 11, USA). Cox regression of the log hazard ratio on HAGE covariant (SD=0.728) based on a sample of 1671 observations, achieves 90% power at 0.05 significant level to detect a small regression coefficient equal to 0.20 for risk of recurrence and death.

Results

A) Clinicopathological Significance of HAGE Expression

Normal breast terminal duct lobular units (TDLUs) showed HAGE− expression throughout. A total of 1671 tumours were suitable for analysis of HAGE expression. 137/1671(8%) of the tumours were found to be HAGE+ using the over 10% cut-off (FIG. 1).

In invasive BC, HAGE+ expression was significantly associated with aggressive/high proliferative clinico-pathological features (Table 1) including; high grade, high mitotic rate, nuclear pleomorphism, TNP and overexpression of both HER2 (adjusted $p$ values<0.0001) and EGFR (p=0.007); Table 1. In addition, abnormal expression of tumour suppressor proteins such as p53 (p=0.03) and p16 (p=0.002) was more common in BC with HAGE+ expression compared to HAGE− tumours. HAGE+ was also associated with Ki67 (p=0.027), KIF2C (p=0.002) and SPAG5 (p=0.004). Notably, HAGE+ expression was also significantly associated with the pro-apoptotic proteins: Bax (p=0.003) and absence of anti-apoptotic Bcl2 protein (p<0.0001). Interestingly, none of the invasive lobular carcinomas were HAGE+(0/154) compared to 10% (124/1285) of non-lobular carcinomas (p<0.0001). In the multivariate logistic analysis, high level of mitosis [OR (95% CI); 1.5 (1.10-1.98), p=0.018], low anti apoptotic Bcl2 [OR (95% CI); 0.33 (0.20-0.56), p<0.0001] and high pro-apoptotic Bax [OR (95% CI); 2.4 (1.52-3.93), p<0.0001] were independent predictor for HAGE+ expression.

B) Survival Analyses

HAGE+ expression in BC tumours showed an adverse outcome at 10 years with a 2-fold increase in the risk of death (HR: 2.4, 95% CI: 1.8-3.1, p<0.0001), recurrence (HR: 2.5, 95% CI: 2.0-3.2, p<0.0001) and DM (HR: 2.3, 95% CI: 1.8-2.9, p<0.0001) compared to tumours with weak HAGE expression (FIG. 2, A1-3). Investigating the clinical outcome of 875 patients with early stage tumours confirmed that tumours with HAGE+ expression displayed a worse prognosis than those with HAGE− expression (FIG. 2, B1-3).

Multivariate Cox Regression Analysis:

In a multivariate Cox regression model which included other validated prognostic factors; lymph node (LN) stage, histological grade, ER status and tumour size; HAGE expression was confirmed as a powerful independent predictor for clinical outcome in the study cohort BC patients (HR: 1.53, 95% CI 1.37-1.71, p<0.0001 (Table 2), along with LN-stage and Bcl2.

Prognostic significance of HAGE expression in low risk patients who did not receive AT:

The expression of HAGE on the survival of low risk BC patients (NPI<3.4), treated with surgery followed by radiotherapy only (n=368) was assessed. At 10 years, HAGE+ expression showed a 4-5 fold increase in the risk of death (HR: 5.1, 95% CI: 2.6-11.2, p<0.0001), recurrence (HR: 3.7, 95% CI: 2.0-6.8, p<0.0001) and DM (HR: 3.8, 95% CI: 1.8-8.0, p=0.001) compared to HAGE− expression. Notably, the 10-year survival probability of low risk BC patients with HAGE− expression was 94% which is indistinguishable from that of age-matched females without BC.

Prognostic significance of HAGE expression in ER+ high risk BC patient who received ET:

Patients whose tumours were categorised as high risk (NPI≥3.4)/ER positive who received ET with HAGE+ expression had a 3-fold increase in risk of death (HR: 3.0, 95% CI: 2.1-4.4, p<0.0001), recurrence (HR: 2.9, 95% CI: 2.1-4.1, p<0.0001) and DM (HR: 2.7, 95% CI: 1.9-3.9, p<0.0001) at 10 years compared with patients whose tumours displayed HAGE− expression (FIG. 3, A1-3).

Prognostic significance of HAGE expression in high risk/ER negative BC received No CT The poor clinical outcome of BC with HAGE+ expression was further confirmed in high risk (NPI>3.4) ER negative patients who did not received any chemotherapy (n=300; FIG. 3, B1-3). At 10 years, patients whose tumours showed HAGE+ expression had 2-4 fold increase in the risk of death (HR: 4.0, 95% CI: 2.6-6.5, p<0.00001), recurrence (HR: 3.4, 95% CI: 2.2-5.2, p<0.00001) and DM (HR: 2.1, 95% CI: 1.5-3.1, p<0.00001) compared to those with HAGE− expression.

Clinical outcome of HAGE expression in high risk/ER negative BC received CMF-CT

Interestingly, in high risk ER negative BC (n=270) who did receive CMF, HAGE+ expression has no statistically significant difference of increased risk of death, recurrence or distant metastases from those with HAGE− expression (FIG. 3, C1-3). This would suggest a beneficial effect of chemotherapy even in the most basic form, and not in the most intensive/efficacy regimen in the modern standard.

Clinical outcome of hage expression in high risk/ER negative BC received modern standard anthracycline CT (ACT)

To confirm the above findings, HAGE expression was validated in an independent cohort of 396 ER negative BCs. A total of 346 tumours were suitable for analysis of HAGE expression and 51/346 (15%) of them showed HAGE+ expression. HAGE+ patients who did receive anthracycline combination chemotherapy (n=189) had a similar risk of death, recurrence and distant metastases to those with HAGE-expression. (FIG. 4, B1-3). These results were confirmed when high risk/ER negative BC who received CT either CMF or anthracycline were pooled together (n=459); FIG. 4, C1-3.

Discussion

This is the first study, to the best of our knowledge reporting HAGE expression in primary BC and evaluating its diagnostic and prognostic value as a biomarker. The clinically significant findings of our study are:

(a) HAGE protein in terms of IHC is highly expressed in BCs in comparison with normal tissues;

(b) HAGE+ expression is significantly associated with aggressive clinico-pathological features including high proliferation, triple negative, overexpression of both EGFR and HER2 and abnormal expression of p53 and p16;

(c) HAGE+ expression in BC is a novel independent factor for poor prognosis;

(d) HAGE+ expression identifies a subgroup of ER− BC patients who could benefit from chemotherapy and furthermore due to the selectively higher HAGE protein expression in the tumours compared with normal tissues, this could be explored as a novel immuno-therapeutic target.

Cancer Testis antigens (CTA) are shared by a variety of malignant tumours, but not by normal tissues with the exception of germ cells in the testis. The restricted expression by neoplastic tissues and inherent immunogenic features make CTA ideal markers for immunotherapy 6. In the current study HAGE+ expression was observed in about 10% of BC compared to matched-adjacent normal tissue and there was a 2-fold increase in the risk of recurrence and DM. This suggests that HAGE could be an oncogene with an important role in BC development and progression. In various haematological and solid tumours including BC 6-8, HAGE has been shown to be over-expressed at both mRNA and protein level at varying frequencies compared to matched normal tissue with exception of testes. Moreover, in agreement with previous studies on other CTA[20-23], we have found that HAGE+ expression was associated with less-differentiated, higher-grade tumours and worse outcome. However, the exact molecular mechanisms which operate to increase HAGE and other CTA protein expression in human cancer remain unclear. There is substantial evidence that epigenetic events appear to represent the unique mechanism regulating the expression of CTA in cancer cells and global DNA methylation seems to play a major role 19. In chronic myeloid leukaemia (CML) and in cell lines it has been shown that, hypomethylation of the HAGE gene promoter correlated with increased HAGE expression which was strongly associated with advanced disease and poor prognosis. This supports the potential role of HAGE in increased cellular proliferation and/or survival and its potential as a marker of disease progression 20. Interestingly, the global hypo-methylation of DNA and histones has been shown to increase progressively in parallel to advanced grade and progression in breast, ovarian, cervical, neural, lung and CML cancers[24-27]

The precise function of HAGE in human cancer remains unknown. We have recently confirmed that HAGE is involved in promoting proliferation as assessed by increased thymidine incorporation. Cells, not naturally expressing HAGE and transfected with the cDNA encoding HAGE increased their proliferation, while cells, naturally expressing HAGE and treated with specific HAGE siRNA significantly decreased their proliferation rate (Linley et al manuscript in preparation). Moreover, preliminary results using shRNA to permanently knockdown HAGE expression also suggests the involvement of HAGE in tumour motility and metastasis (data not shown). In addition, it has been recently reported that HAGE could be involved in both altered gene expression and RNA editing[20]. In fact, the protein encoded by the HAGE gene is also a member of the family of "DEAD-box proteins" which contain the highly conserved Asp-Glu-Ala-Asp (D-E-A-D) motif and these proteins are involved in many aspects of RNA metabolism, spermatogenesis, embryogenesis, and cell growth, functioning as important transcriptional regulators and suggesting that HAGE may also be an ATP-dependent RNA helicase 20,29, 30. Roman-Gomez J et al 2007 20 have speculated that blast crisis cells of CML that overexpressed HAGE may have a selective advantage over HAGE− cells, which would provide an explanation for why HAGE expression is positively selected during CML progression. However, the possible role of HAGE in the transformed status of BC cells should be clarified in further function studies.

In our study, survival analysis indicates that HAGE is an independent prognostic factor of reduced survival in BC patients (about 10% in our primary series), especially in those with early-stage tumours. This finding is consistent with the finding in CML, where high expression level of HAGE transcripts was associated with poor prognosis[20,31]. Similarly, for a given cancer type, higher expression of some other CTAs is often correlated with worse outcome, such as testes-specific protease 50 (TSP 50) for colorectal[32], MAGE-A3 for pancreatic cancer[33], MAGE-C2 for hepatocellular carcinoma[34] and NY-ESO-1 for malignant melanoma[35]. Recently, Germain et al 2011[35] have found that mRNA expression of DEAD-box 1 is an independent prognostic marker for early recurrence in BC. Moreover, DEAD-box proteins have been reported to be overexpressed in retinoblastoma and neuroblastoma cell lines and in up to 76% of BC[36,37] and have been shown to be co-activators of ER.

HAGE expression may be a useful tool in the stratification of BC patients for AT. Our data suggests that otherwise low risk (NPI<3.4) HAGE+ tumours should be included within high risk groups and would benefit from AT. Moreover, poor clinical outcome with HAGE+ expression was also confirmed in high risk BC, suggesting that alternative aggressive AT may be warranted in this group. Importantly our results showed ER negative patients who received CMF had indistinguishable clinical outcome for high and low HAGE expression suggesting that patients with HAGE+ may gain some benefit from CMF chemotherapy. These results were further validated in an independent cohort of ER negative tumours which confirmed the initial findings. It can be proposed that cells expressing HAGE proliferate faster and are therefore more responsive to ACT targeting highly proliferative cells such as CMF or FEC. In fact recent studies[32] reported that knockdown of TSP50 gene expression inhibited cell proliferation, colony formation and migration; and also induced cell apoptosis and enhanced cell sensitivity to doxorubicin.

Furthermore, given that HAGE-antigen is immunogenic, it could be a potentially therapeutic target for CTA-based cancer vaccines in late stages of BC. The DNA methyltransferase inhibitor 5-aza-2'-deoxycytidine (decitabine) has been shown to be beneficial for CML patient[38]. These drugs, that are capable of inducing HAGE expression, could increase patient eligibility and treatment effectiveness in CTA-targeted immunotherapy and improve our therapeutic gain in terms of prevention of tumour recurrence.

In conclusion, HAGE is a potentially effective prognostic marker which predicts poor prognosis in a sub-group of BCs patients who have high expression of the protein as measured by IHC and may be an attractive novel target for molecular and vaccine therapy for those patients. A prospective trial of adjuvant chemotherapy/vaccine to confirm this finding is warranted.

Further Work

Materials and Methods

Study populations

The inventors retrospectively identified 599 consecutive patients who were treated for TNBC in Nottingham, United Kingdom, between 1986 and 2010 and were suitable for HAGE immunohistochemistry staining.

A) Early primary triple negative breast cancer (EP-TNBC; n=520)

Of these patients 520 had EP-TNBC; 297 cases did not receive any chemotherapy, either because the patient declined systemic treatment, adjuvant chemotherapy was not the standard of care at that time, or patients were of low risk [Nottingham Prognostic Index (NPI)≤3.4] and 225 cases are of high risk (NPI>3.4) and received adjuvant chemotherapy (ACT). 114 patients were treated before 2000 and received CMF combination therapy (cyclophosphamide, methotrexate and 5-fluorouracil) and 111 who treated after 2000 were received anthracycline combination ACT (ATC-ACT. The decision to give chemotherapy was based on the patients' risk as predicted by the NPI, ER, and menopausal status [11].

B) Primary locally advanced breast cancer (PLA-TNBC; n=79)

In addition, 79 patients with PLA-TNBC (stage IIIA-C) were treated with ATC-ACT. Response to ATC-ACT was recorded. A pathological complete response (pCR) was defined as an absence of any residual invasive carcinoma at both the primary site and in axillary lymph nodes (LNs). On an average, 16 breast blocks and all submitted LNs were examined for each case before a diagnosis of pCR was reached. Detailed patient demographics and clinico-pathological characteristics were routinely assessed and regularly updated.

Survival data

Survival data including survival time, disease-free survival (DFS), and development of loco-regional and distant metastases (DM) were maintained on a prospective basis. DFS was defined as the number of months from diagnosis to the occurrence of recurrence or DM relapse. BC specific survival (BCSS) was defined as the number of months from diagnosis to the occurrence of BC related-death. Survival was censored if the patient was still alive, lost to follow-up, or died from other causes.

The Reporting Recommendations for Tumor Marker Prognostic Studies (REMARK) criteria [12] were followed throughout this study.

This work was approved by Nottingham Research Ethics Committee.

Tissue Microarrays (TMAs) and immunohistochemistry (IHC)

Tumors from both EP-TNBC and PLA-TNBC post-surgical specimens were arrayed in tissue microarrays (TMAs) constructed with 6 replicate 0.6 mm cores from the centre and periphery of the tumors for each patient. In addition, for PLA-TNBC cases that were treated with ATC-ACT, full-face sections from the diagnostic pre-chemotherapy core biopsy were used. The TMAs and full face sections were immunohistochemically profiled for HAGE and other biological antibodies as previously described [14]. Immunohistochemical staining was performed using NOVOLINK Detection kit according to the manufacturer instructions (Leica Microsystems). TMA sections were incubated overnight at room temperature with 1/175 Anti-HAGE rabbit polyclonal mono-specific antibody (custom made) [6]. In addition we validated our results using a commercially available antibody that was developed and validated by Human Protein Atlas (HPA) project (anti DDX43; HPA031381, Sigma-Adrich). Pre-treatment of TMAs section was performed with citrate buffer (pH 6.0) antigen for 20 minutes.

HER2, ER and PR expressions were assessed according to the new American Society of Clinical Oncology/College of American Pathologists (ASCO/CAP) guidelines 18-19. HER2 status was assessed using both IHC and fluorescence in situ hybridization (FISH) as previously described, Wolff A C et al, J. Clin. Oncol. (2007) 25: 118-145.

To validate the use of TMAs for immuno-phenotyping, full-face sections of 40 cases were stained and the protein expression levels of the different antibodies were compared. The concordance between TMAs and full-face sections was excellent (kappa=0.8). Positive and negative (omission of the primary antibody and IgG-matched serum) controls were included in each run.

Evaluation of HAGE immunohistochemical staining

The tumor cores were evaluated by three pathologists of co-authors blinded to the clinico-pathological characteristics of patients in two different settings. There was excellent intra and inter-observer agreements (k>0.8; Cohen's κ and multi-rater κ tests, respectively). Whole field inspection of the core was scored and intensities of both nuclear and cytoplasmic staining were grouped as follows: 0=no staining, 1=weak staining, 2=moderate staining, 3=strong staining. The percentage of each category was estimated. High HAGE (HAGE+) expression was defined as the presence of strong cytoplasmic and/or nuclear staining in >10% of malignant cells (FIG. 5-A). Not all cores within the TMA were suitable for IHC analysis as some cores were missing or lacked tumor.

Statistical analysis: Data analysis was performed using SPSS (SPSS, version 17 Chicago, Ill.). Where appropriate, Pearson's Chi-square, Fisher's exact, and Student's tests were used. Positivity for HAGE protein both pre- and post-chemotherapy were calculated and compared using McNemar's test. Significance was defined at $p<0.05$.

Cumulative survival probabilities were estimated using the Kaplan-Meier method, and differences between survival rates were tested for significance using the log-rank test. Multivariate analysis for survival was performed using the Cox proportional hazard model. The proportional hazards assumption was tested using standard log-log plots. Hazard ratios (HR) and 95% confidence intervals (95% CI) were estimated for each variable. All tests were two-sided with a 95% CI and a p value<0.05 considered significant. For multiple comparisons, a stringent p value<0.01 was considered significant.

Results

1: EP-TNBC cohort

EP-TNBC patients were all female and their median age was 51 years (range 28-71 years). Their median follow up was 107 months (range 2-243 months). All of them underwent standard surgery (mastectomy or wide local excision) with or without adjuvant or chemotherapy. Each patient's tumour was ER negative, PR negative and HER2 negative.

1A: Clinico-pathological features of HAGE expression in EP-TNBC

Positive HAGE expression (HAGE+; FIG. 5 Panels B-D) was observed in 77/520 (14.8%) of EP-TNBC tumours and was more common in postmenopausal TNBC (p=0.010). HAGE+ was significantly associated with none-lobular carcinoma (p=0.001), high expression of androgen receptor, (AR; p=0.008), FEN1 cytoplasmic expression (p=0.00008), cell cycle arrest protein p21 (p=0.0009) and pro-apoptotic Bax (p=0.01) as well as loss of anti-apoptotic Bcl2 (0.001) [Table 3]. Multivariate logistic regression confirmed that FEN1 (OR=3.0, p=0.007), Bax [OR=8.7, p=0.003, p21 (OR=5.6, 0.028) and menopausal status (OR=5.8, p=0.027) were independently associated with HAGE+ expression.

1B: HAGE is an independent prognostic biomarker in PO-TNBC

In univariate analysis, HAGE+ was strongly associated with an adverse outcome at 10 years and had increased risk of death from EP-TNBC (HR: 1.3; 95% CI: 1.2-1.5; p=0.000005) and recurrence (HR: 1.2; 95% CI: 1.1-1.4; p=0.0003); (FIGS: 5-B). HAGE was confirmed as an independent prognostic factor after controlling for chemotherapy and other validated prognostic factors: stage, grade, size, menopausal status and Bcl2 (Table 4). Chemotherapy, HAGE, Bcl2- and Lymph node stage were independently predictive of both poor DFS and BCSS at 10 year (Table 4). HAGE+ were associated with double risk of death (HR: 2.1; 95% CI: 1.5-3.1; p=0.00007) and recurrence (HR: 1.6; 95% CI: 1.2-2.5; p=0.002).

1C: HAGE positive EP-TNBC gained benefit from adjutant chemotherapy

The EB-TNBC cohort was further subdivided into 2 patient groups based on the chemotherapy given: i) no chemotherapy (FIG. 5C), and ii) received chemotherapy either CMF or anthracycline-combination (FEC-5FU, epirubicin, cyclophosphamide) (FIG. 5 D). Again HAGE+ was associated with higher risk of death from EP-TNBC (HR: 1.4; 95% CI: 1.2-1.7; p=0.0000004) and also of recurrence (HR: 1.3; 95% CI: 1.1-1.5; p=0.00007) in patients who did not receive chemotherapy (FIG. 5 C). While, in EP-TNBC patients who received chemotherapy, HAGE+ tumours had a clinical outcome similar to those with HAGE− phenotype (FIG. 5 D).

2: PLA-TNBC patients treated with ATC-ACT

All LA-TNBC patients were female and their mean age was 51 years (range 25-76 years). All patients received ATC_ACT either without (52/79; 65.8%) or with (27/79; 34.2%) Taxane. 52/79 (65.8%) of patients received six cycles of an anthracycline-based-therapy (FEC: 5-fluorouracil (5-FU) 500 mg m$^{-2}$, epirubicin 75-100 mg m$^{-2}$, cyclophosphamide 500 mg m$^{-2}$, on day 1 of a 21-day cycle). Patients were scheduled to undergo surgery 4 weeks after the sixth cycle. All of them underwent surgery followed by radiotherapy with (21.5%) or without chemotherapy (78.5%). 14/79 (17.7%) of P LA-TNBC patients achieved pCR. 40.5% of PLA-TNBC displayed HAGE+ expression in pre-chemotherapy diagnostic core biopsy, while only 20% of post-chemotherapy specimens showed HAGE+ expression.

1a. Pre-chemotherapy HAGE expression is a predictor of pCR rate for ATC_ACT 10/32 (31%) of PLA-TNBC with HAGE+ in pre-chemotherapy core biopsies, achieved-pCR after ATC-ACT vs., only 4/47 (8%) of those with HAGE− (p=0.009), Table 5. After receiving ATC-ACT, PLA-TNBC with HAGE+ expression in pre-chemotherapy biopsies [19/32 (59%)] have converted into either HAGE− or achieved pCR and 13/32 (41%) retained their HAGE+ expression in post-chemotherapy samples (McNemar test, p=0.001).

Multivariate logistic regression analysis after controlling to age at diagnosis, grade, tumour stage, and prechemotherapy tumour size showed that pre-chemotherapy HAGE+ expression is an independent predictor of pCR of PLA-TNBC [OR (95% CI)=2.28 (1.1-4.7), p=0.027]; (Table 6).

PLA-TNBC patients who received ATC-ACT and had a pre-chemotherapy HAGE+ expression had a risk of death (p=0.322) and progression (p=0.529) similar to those with HAGE− PLA-TNBC patients; FIG. 6-A1-2). While, among the PLA_TNBC patients who had residual disease and who after ATC-ACT retained HAGE+ expression (16/65; 25%) had a worse BCSS [2.82 (1.3-6.1), p=0.009] and DFS [2.96 (1.4-6.2), p=0.004] compared to those with HAGE− expression (FIG. 6 B-1-2).

Discussion

TNBC encompasses a subpopulation of BC patients traditionally considered to have a poor prognosis, Dent R et al, Clin. Cancer Res. (2007) 13; 4429-34. Neither the classical pathological variables nor the modern molecular assays, have shown prognostic value in this patient group. Though a wide variety of tumors have been studied, knowledge about presence of CTAs on a protein level in TNBC is comparably limited. To the best of our knowledge this is the first study to report on HAGE expression in TNBC and evaluate its prognostic and predictive value. The results of our study show HAGE to be a promising prognostic and predictive biomarker for TNBC. Considering the limited treatment options for TNBC, combined chemo-immunotherapy should be explored in more details as a target therapeutic option for TNBC patients.

In the current study, high levels of HAGE expression was observed in 15% of patients with TNBC and was associated with increased risk of recurrence and metastases. HAGE has been shown to be over-expressed at both the mRNA and protein level at varying frequencies in different human tumors compared to matched normal tissue with exception of testes. In addition, few recent studies suggested an elevated expression of CTAs in TNBC and high grade BC especially MAGE-A and NY-ESO-1. In our study, survival analysis indicates that HAGE is an independent prognostic factor for TNBC patients. This finding is consistent with the finding in leukaemia, in which HAGE+ transcripts have been associated with poor prognosis. Similarly, for a given cancer type, higher expression of some other CTAs such as testes-specific protease 50 (TSP 50) for colorectal, MAGE-A3 for pancreatic cancer, MAGE-C2 for hepatocellular carcinoma and NY-ESO-1 for malignant melanoma is often correlated with worse outcome. However, most of these studies were focused on messenger RNA expression and their IHC data were restricted to a small number of patients and lack of power.

The early identification of features associated with response or resistance to primary neoadjuvant therapy is important in the development of the most effective multimodal approaches and identifying cohorts of patients most likely to benefit from chemotherapy. Pathological complete remission (pCR) rate are significantly higher following neoadjuvant chemotherapy for patients with TNBC. Regardless of the higher likelihood of pCR for patients with TNBC disease, the 5-year disease-free survival is significantly worse for this cohort compared with the ER-positive cohort in several studies. Importantly, patients with ER-positive residual tumors have remarkably better survivals than patients with ER-negative tumors not achieving a pCR, Guarneri V et al, Ann. Oncol. 2009, 20: 1193-1198.

HAGE expression may be a useful tool for the stratification of patients with breast cancer for chemotherapy. Our data show that HAGE+ patients may benefit from neoadjuvant ACT. The explanation behind this finding is likely to be complex. In our TNBC cohort, we found HAGE+ was associated with loss of anti-apoptotic Bcl2 factor, high level of pro-apoptotic Bax protein and high level of cell cycle arrest p21 protein (G0/G1 check protein). Therefore HAGE+ cells are more likely to respond to DNA damage treatment, probably through accumulation of DNA damage, abnormal mitoses and subsequent mitotic catastrophe. The mechanisms of mitotic catastrophe are unknown, but it likely results from a combination of deficient cell-cycle checkpoints (in particular the DNA structure checkpoints and the spindle assembly checkpoint) and cellular damage catastrophe. Conversely, non-responding HAGE+ tumours could escape the response through accumulation of genetic abnormalities that would not lead to a mitotic catastrophe but rather to aneuploidy and subsequent growth advantage.

Previous studies have suggested that a subset of TNBC expressed AR and this ER-/PR-/AR+ breast tumors may benefit from hormone manipulation which targets androgen such as Bicalutamide rather than oestrogen. Given that our results showed that HAGE+ was associated with AR+ in TNBC, this approach could benefit that subset of TNBC population which has not benefited from available therapies.

Recently we conducted gene and proteins expression analysis of FEN1 in BC and ovarian cancers and our data provides evidence that FEN1 is a key biomarker as well as a drug target. In this study, we demonstrated that in cancer cell lines, FEN1 depletion or FEN1 inhibition by a small molecule results in sensitivity to DNA damaging chemotherapy such anthracycline and cis-platinum. In addition by using a high throughput screening of 391,275 compounds we have uncovered novel FEN1 inhibitors. Thus the association between HAGE+ and FEN1+ could explained why HAGE+/TNBC had higher response rate to anthracycline and FEN1 inhibitors could be explored in those with HAGE+/FEN1+ who had residual disease after neoadjuvant ACT.

Moreover, the fact that patients with HAGE+ residual disease (ACT-resistant cells) have a poorer outcome suggest that alternative therapy such as immunotherapy may be warranted for this group. Given that HAGE antigen is immunogenic, one should consider targeting HAGE along with other CTA using immunotherapeutic intervention in conjunction with chemotherapy for TNBC Recently, understanding of the interaction between the tumor and immune system has led to the development of novel immunotherapies, including cancer vaccines. However; cancer vaccines had a poor clinical track record due to poor clinical results of so many promising vaccines. However; in recent trials using immunotherapy, clinical outcomes have shown improved PFS or OS (compared to historical controls), Kyte J A et al, Clin. Cancer Res. (2011) 17, 4568-4580; Slingloff C L et al, J. Clin. Oncol. 2011 10-1200/JCO 2010-33. 8053; Neninger E et al J. Immunother; 2009; 32; 92-99; Sampson J H et al Neuro. Oncol. 2010, 13, 324-333; Zhou et al J. Exp. Clin. Cancer Res. 2011 20: 2. It had been generally assumed that immune-stimulatory cancer vaccines could not be used in combination with immunosuppressive chemotherapies, but recent evidence has challenged this dogma. In fact, chemotherapies could be used to condition the immune system and tumor to create an environment where cancer vaccines have a better chance of success by lowering the defences of the tumor either by (1) targeting the immune system to reduce tumor-induced immune suppressive cells; (2) targeting the tumor to increase immunogenicity (increase MHC or antigen expression); (3) directly stimulating effector response by activating T cells (reviewed by Weir G M, Cancers 2011; 3; 3114-3142). For instance, Zitvogel et al have highlighted the fact that anthracyclines unlike many other cytotoxic agents can elicit immunogenic cell death and that when given before immunisation can potentiate the effect of the vaccine, Nat. Rev. Immunol. 2008; 8; 59-73. Furthermore, The DNA methyltransferase inhibitor 5-aza-2'-deoxycytidine (decitabine) has been shown to be beneficial for patients with chronic myeloid leukaemia (CML) [38]. Drugs such as decitabine that is capable of inducing HAGE expression could therefore increase the eligibility of patients for CTA-targeted immunotherapy and improve the management of patients with recurrent disease.

Our study also highlights the need for alternative treatment strategies in patients with TNBC/HAGE- tumors, since responses to ACT were preferentially observed when HAGE is expressed. Further work aimed at identifying markers that are over-expressed in this patient group (e.g. other TSA) which could serve as potential therapeutic targets is required.

In conclusion, this study demonstrates that the expression of HAGE is a potential prognostic marker of outcome as well as a predictor of response to anthracycline treatment in TNBc.

REFERENCES

1. Gluck S, Mamounas T: Improving outcomes in early-stage breast cancer. Oncology (Williston Park) 24:1-15

2. Clarke M, Coates A S, Darby S C, et al: Adjuvant chemotherapy in oestrogen-receptor-poor breast cancer: patient-level meta-analysis of randomised trials. Lancet 371:29-40, 2008
3. Dotan E, Goldstein L J: Optimizing chemotherapy regimens for patients with early-stage breast cancer. Clin Breast Cancer 10 Suppl 1:E8-15
4. Harris L, Fritsche H, Mennel R, et al: American Society of Clinical Oncology 2007 update of recommendations for the use of tumour markers in breast cancer. J Clin Oncol 25:5287-312, 2007
5. Harbeck N, Salem M, Nitz U, et al: Personalized treatment of early-stage breast cancer: present concepts and future directions. Cancer Treat Rev 36:584-94
6. Mathieu M G, Linley A J, Reeder S P, et al. HAGE, a cancer/testis antigen expressed at the protein level in a variety of cancers. Cancer Immunity 2009.
7. Martelange V, De Smet C, De Plaen E, et al: Identification on a Human Sarcoma of Two New Genes with Tumor-specific Expression. Cancer Research 60: 3848-3855, 2000.
8. Adams S P, Sahota S S, Mijovic A, et al. Frequent expression of HAGE in presentation chronic myeloid leukaemias. Leukemia 16(11):2238-42, 2002.
9. Mathieu M G, Knights A J, Pawelec G, et al. HAGE, a cancer/testis antigen with potential for melanoma immunotherapy: identification of several MHC class I/II HAGE-derived immunogenic peptides Cancer ImmunolImmunother 56:1885-1895, 2007.
10. Pinder S E, Ellis I O, Galea M, et al: Pathological prognostic factors in breast cancer. III. Vascular invasion: relationship with recurrence and survival in a large study with long-term follow-up. Histopathology 24:41-7, 1994
11. Elston C W, Ellis I O: Pathological prognostic factors in breast cancer. I. The value of histological grade in breast cancer: experience from a large study with long-term follow-up. Histopathology 19:403-10, 1991
12. McShane L M, Altman D G, Sauerbrei W, et al: Reporting recommendations for tumour marker prognostic studies (REMARK). J Natl Cancer Inst 97:1180-4, 2005
13. Abdel-Fatah T M, Powe D G, Ball G, et al: Proposal for a modified grading system based on mitotic index and Bcl2 provides objective determination of clinical outcome for patients with breast cancer. J Pathol 222:388-99, 2010
14. Abdel-Fatah T M, Powe D G, Agboola J, et al: The biological, clinical and prognostic implications of p53 transcriptional pathways in breast cancers. J Pathol 220: 419-34, 2010
15. Callagy G M, Pharoah P D, Pinder S E, et al: Bcl-2 is a prognostic marker in breast cancer independently of the Nottingham Prognostic Index. Clin Cancer Res 12:2468-75, 2006
16. Tan D S, Marchio C, Jones R L, et al: Triple negative breast cancer: molecular profiling and prognostic impact in adjuvant anthracycline-treated patients. Breast Cancer Res Treat 111:27-44, 2008
17. Sauter G, Lee J, Bartlett J M, et al: Guidelines for human epidermal growth factor receptor 2 testing: biologic and methodologic considerations. J Clin Oncol 27:1323-33, 2009
18. Holm S: A simple sequentially rejective multiple test procedure. Scand J Stat 6:65-70., 1979
19. Lurquin C, Lethe B, De Plaen E, et al: Contrasting frequencies of antitumor and anti-vaccine T cells in metastases of a melanoma patient vaccinated with a MAGE tumour antigen. J Exp Med 201:249-57, 2005
20. Roman-Gomez J, Jimenez-Velasco A, Agirre X, et al: Epigenetic regulation of human cancer/testis antigen gene, HAGE, in chronic myeloid leukaemia. Haematologica 92:153-62, 2007.
21. Otte M, Zafrakas M, Riethdorf L, et al: MAGE-A gene expression pattern in primary breast cancer. Cancer Res 61:6682-7, 2001.
22. Kurashige T, Noguchi Y, Saika T, et al: NY-ESO-1 expression and immunogenicity associated with transitional cell carcinoma: correlation with tumour grade. Cancer Res 61:4671-4, 2001.
23. Yakirevich E, Sabo E, Lavie O, et al: Expression of the MAGE-A4 and NY-ESO-1 cancer-testis antigens in serous ovarian neoplasms. Clin Cancer Res 9:6453-60, 2003.
24. Kim Y I, Giuliano A, Hatch K D, et al: Global DNA hypomethylation increases progressively in cervical dysplasia and carcinoma. Cancer 74:893-9, 1994
25. Qu G, Dubeau L, Narayan A, et al: Satellite DNA hypomethylation vs. overall genomic hypomethylation in ovarian epithelial tumours of different malignant potential. Mutat Res 423:91-101, 1999.
26. Soares J, Pinto A E, Cunha C V, et al: Global DNA hypomethylation in breast carcinoma: correlation with prognostic factors and tumour progression. Cancer 85:112-8, 1999.
27. Piyathilake C J, Frost A R, Bell W C, et al: Altered global methylation of DNA: an epigenetic difference in susceptibility for lung cancer is associated with its progression. Hum Pathol 32:856-62, 2001.
28. Zhou L, Bao Y L, Zhang Y, Wu Y, Yu C L, et al: Knockdown of TSP50 inhibits cell proliferation and induces apoptosis in P19 cells. IUBMB Life 62:825-832, 2010.
29. Iggo R, Picksley S, Southgate J, et al: Identification of a putative RNA helicase in E. coli. Nucleic Acids Res 18:5413-7, 1990
30. Yang L, Lin C, Liu Z R: Phosphorylations of DEAD box p68 RNA helicase are associated with cancer development and cell proliferation. Mol Cancer Res 3:355-63, 2005.
31. Chen Q, Lin J, Qian J, Yao D M, et al: Gene expression of helicase antigen in patients with acute and chronic myeloid leukaemia. Zhongguo Shi Yan Xue Ye XueZaZhi. 19:1171-5, 2011
32. Zheng L, Xie G, Duan G, et al: High expression of testes-specific protease 50 is associated with poor prognosis in colorectal carcinoma. PLoS One 6:e22203, 2011
33. Kim J, Reber H A, Hines O J, et al: The clinical significance of MAGEA3 expression in pancreatic cancer. Int J Cancer 118:2269-2275, 2006
34. Riener M O, Wild P J, Soll C, et al: Frequent expression of the novel cancer testis antigen MAGE-C2/CT-10 in hepatocellular carcinoma. Int J Cancer 124: 352-357, 2009
35. Velazquez E F, Jungbluth A A, Yancovitz M, et al.: Expression of the cancer/testis antigen NY-ESO-1 in primary and metastaticmalignant melanoma (MM)-correlation with prognostic factors. Cancer Immun 7: 11,
36. Shin S, Rossow K L, *Grande* J P, et al: Involvement of RNA helicases p68 and p72 in colon cancer. Cancer Research 67:7572-7578, 2007.
37. Wortham N C, Ahamed E, Nicol S M, et al: The DEAD-box protein p72 regulates ER alpha-/oestrogen-dependent transcription and cell growth, and is associated with improved survival in ER alpha-positive BC. Oncogene; 28:4053-4064, 2009.

38. Issa J P, Garcia-Manero G, Giles F J, et al: Phase 1 study of low-dose prolonged exposure schedules of the hypomethylating agent 5-aza-2'-deoxycytidine (decitabine) in hematopoietic malignancies. Bloood 103:1635-40, 2004

Tables

TABLE (1)

Association between HAGE expression and other clinico-pathologic variables

| | HAGE Expression | | |
|---|---|---|---|
| Variable | Loss (N = 1581) n (%) | Positive (N = 134) n (%) | $X^2$ Adjusted p value |
| A) Pathological Parameters | | | |
| Tumor Size | | | NS |
| T1 a + b (≤1.0) | 140 (11) | 7 (9) | |
| T1 c (>1.0-2.0) | 692 (52) | 70 (56) | |
| T2 (>2.0-5) | 471 (36) | 48 (38) | |
| T3 (>5) | 16 (1) | 0 (0) | |
| Lymph node stage | | | NS |
| Negative | 836 (63) | 78 (62) | |
| Positive (1-3 nodes) | 397 (30) | 39 (31) | |
| Positive (>3 nodes) | 89 (7) | 62 (7) | |
| Grade** | | | $2.3 \times 10^{-6}$* |
| G1 | 246 (18) | 15 (12) | |
| G2 | 444 (34) | 24 (19) | |
| G3 | 629 (48) | 86 (69) | |
| Tumor Types | | | $5.5 \times 10^{-5}$* |
| ILC | 154 (22) | 0 (0) | |
| Non-lobular carcinoma | 1161 (88) | 124 (100) | |
| Mitotic Index | | | $2.3 \times 10^{-6}$* |
| M1 (low; mitoses <10) | 509 (39) | 21 (17) | |
| M2 (medium; mitoses 10-18) | 242 (18) | 24 (19) | |
| M3 (high; mitosis >18) | 568 (43) | 80 (64) | |
| Pleomorphism | | | 0.005* |
| 1 (small-regular uniform) | 38 (3) | 3 (3) | |
| 2 (Moderate variation) | 541 (41) | 33 (26) | |
| 3 (Marked variation) | 740 (56) | 89 (71) | |
| B) Hormonal receptors | | | |
| ER (Negative) | 316 (26) | 51 (45) | $1.7 \times 10^{-5}$* |
| (Positive) | 891 (74) | 62 (55) | |
| PR (Negative) | 533 (43) | 67 (56) | 0.004* |
| (Positive) | 714 (57) | 52 (44) | |
| Cell cycle/apoptosis regulators | | | |
| p53 (Negative) | 979 (80) | 81 (72) | 0.03* |
| (Positive) | 242 (20) | 32 (28) | |
| EGFR (Negative) | 951 (81) | 78 (70) | 0.007* |
| (Positive) | 224 (19) | 33 (30) | |
| Bax (Negative) | 625 (71) | 45 (55) | 0.002* |
| (Positive) | 253 (29) | 37 (45) | |
| Bcl2 (Negative) | 445 (32) | 67 (52) | $6.2 \times 10^{-6}$ |
| (Positive) | 923 (68) | 61 (48) | |
| Ki67 (Negative) | 356 (47) | 26 (32) | 0.01* |
| (Positive) | 402 (53) | 54 (68) | |
| p16 (Negative) | 915 (87) | 81 (76) | 0.002* |
| (Positive) | 132 (13) | 25 (24) | |
| Aggressive phenotype | | | |
| Her2 overexpression (No) | 1307 (88) | 101 (74) | $1.3 \times 10^{-5}$* |
| (Yes) | 185 (12) | 35 (26) | |
| Triple negative (No) | 1077 (84) | 90 (75) | 0.016* |
| (Yes) | 210 (16) | 30 (25) | |
| Basal like (No) | 1094 (87) | 89 (79) | 0.013* |
| (Yes) | 162 (13) | 24 (21) | |

*Statistically significant;
**grade as defined by NGS; BRCA1: BC 1, early onset; HER2: human epidermal growth factor receptor 2; ER: oestrogen receptor; PR: progesterone receptor; CK: cytokeratin; Basal-like: ER−, HER2 and positive expression of either CK5/6, CK14 or EGFR; Triple negative: ER−/PR−/HER2−

TABLE (2)

Multivariate analysis using Cox regression analysis confirms that HAGE protein expression is independent prognostic factor

| | Variable | | | | | |
|---|---|---|---|---|---|---|
| | BCSS | | DFS | | DM-FS | |
| | HR (CI 95%) | p | HR (CI 95%) | p | HR (CI 95%) | p |
| HAGE (positive) | 2.1 (1.6-2.7) | $5.2 \times 10^{-8}$** | 2.3 (1.8-2.9) | $2.1 \times 10^{-13}$** | 2.0 (1.5-2.5) | $1.6 \times 10^{-7}$** |
| Tumor size | 1.4 (1.2-1.5) | $4.8 \times 10^{-9}$** | 1.3 (1.2-1.4) | $8.4 \times 10^{-7}$** | 1.4 (1.2-1.5) | $3.6 \times 10^{-9}$** |
| Grade | | $3.2 \times 10^{-14}$** | | 0.001** | | $1.0 \times 10^{-8}$** |
| G1 | 1.0 | | 1.0 | | 1.0 | |
| G2 | 2.0 (1.3-3.1) | | 1.2 (0.9-1.5) | | 1.6 (1.2-2.3) | |
| G3 | 3.8 (2.6-5.7) | | 1.5 (1.2-2.0) | | 2.5 (1.7-3.5) | |
| Lymph node | | $4.8 \times 10^{-9}$** | | $9.4 \times 10^{-16}$** | | $1.6 \times 10^{-8}$** |
| Negative | 1 | | 1 | | 1 | |
| Positive (1-3 nodes) | 1.4 (1.1-1.8) | | 1.2 (1.0-1.5) | | 1.4 (1.2-1.7) | |
| Positive (>3 nodes) | 3.5 (2.6-4.6) | | 3.1 (2.4-4.1) | | 3.7 (2.8-4.9) | |

**Statistically significant
BCSS; BC specific survival,
DFS; disease free survival,
DM-FS: distant metastases,
HR; hazard ratio,
CI; confident interval Supplemental Tables

TABLE (S1)

Clinicopathological characteristics of whole cohort (N = 1650)

| Variable | n* | Cases (%) |
|---|---|---|
| Menopausal status | 1650 | |
| Pre-menopausal | | 612 (37.0) |
| postmenopausal | | 1038 (63.0) |
| Tumor Grade (NGS) | 1650 | |
| G1 | | 306 (18.5) |
| G2 | | 531 (32.2) |
| G3 | | 813 (49.3) |
| Lymph node stage | 1650 | |
| Negative | | 1056 (64.0) |
| Positive (1-3 nodes) | | 486 (29.5) |
| Positive (>3 nodes) | | 108 (6.5) |
| Tumor size (cm) | 1650 | |
| T1 a + b (≤1.0) | | 187 (11.0) |
| T1 c (>1.0-2.0) | | 868 (53.0) |
| T2 (>2.0-5) | | 5729 (35.0) |
| T3 (>5) | | 16 (1.0) |
| Tumor type | 1650 | |
| IDC-NST | | 941 (57) |
| Tubular | | 349 (21) |
| ILC | | 160 (10) |
| Medullary (typical/atypical) | | 41 (2.5) |
| Others | | 159 (9.5) |
| NPI subgroups | 1650 | |
| Excellent PG (2.08-2.40) | Low risk | 207 (12.5) |
| Good PG (2.42-3.40) | | 331 (20.1) |
| Moderate I PG (3.42 to 4.4) | High risk | 488 (29.6) |
| Moderate II PG (4.42 to 5.4) | | 395 (23.9) |
| Poor PG (5.42 to 6.4) | | 170 (10.3) |
| Very poor PG (6.5-6.8) | | 59 (3.6) |
| Survival at 20 years | 1650 | |
| Alive and well | | 1055 (64.0) |
| Dead from disease | | 468 (28.4) |
| Dead from other causes | | 127 (7.6) |
| Adjuvant systemic therapy (AT) | 1602 | |
| No AT | | 665 (42.0) |
| Hormone therapy (ET) | | 642 (41.0) |
| Chemotherapy | | 307 (20.0) |
| Hormone + chemotherapy | | 46 (3.0) |
| HAGE expression | 1650 | |
| No staining (0) | normal | 1581 |
| Strong (+++) | positive | 134 |

*Number of cases for which data were available.
NPI; Nottingham prognostic index,
PG; prognostic group

SUPPLEMENTAL TABLE S2

Clinicopathological characteristics of validation set

| Variable | n* | Cases (%) |
|---|---|---|
| Menopausal status | 383 | |
| Pre-menopausal | | 163 (42.0) |
| postmenopausal | | 224 (58.0) |
| Tumour Grade (NGS) | 385 | |
| G1 | | 1 (0.3) |
| G2 | | 42 (10.6) |
| G3 | | 353 (89.1) |
| Lymph node stage | 395 | |
| Negative | | 250 (63) |
| Positive (1-3 nodes) | | 95 (24) |
| Positive (>3 nodes) | | 50 (13) |
| Tumour size (cm) | 385 | |
| T1 a + b (≤1.0) | | 42 (11) |
| T1 c (>1.0-2.0) | | 161 (42) |
| T2 (>2.0-5) | | 160 (41) |
| T3 (>5) | | 22 (6) |
| Tumour type | 396 | |
| IDC-NST | | 356 (89) |
| Tubular | | 7 (2) |
| ILC | | 11 (3) |
| Medullary (typical/atypical) | | 7 (2) |
| Others | | 15 (4) |
| NPI subgroups | 391 | |
| Excellent PG (2.08-2.40) | Low risk | 0 (0.0) |
| Good PG (2.42-3.40) | | 21 (5.0) |
| Moderate I PG (3.42 to 4.4) | High risk | 147 (38.0) |
| Moderate II PG (4.42 to 5.4) | | 127 (33.0) |
| Poor PG (5.42 to 6.4) | | 62 (10.0) |
| Very poor PG (6.5-6.8) | | 34 (9.0) |
| Survival at 5 years | 389 | |
| Alive and well | | 262 (83.0) |
| Dead from disease | | 112 (29) |
| Dead from other causes | | 5 (1.0) |
| HAGE expression | 346 | |
| Low | | 295 (85) |
| High | | 51 (15) |

*Number of cases for which data were available.
NPI; Nottingham prognostic index,
PG; prognostic group

SUPPLEMENTARY TABLE (S2)

Antigens, primary antibodies, clone, source, optimal dilution and scoring system used for each immunohistochemical marker

| Antigen | Antibody | Clone | Source | Dilution | Distribution | Scoring system | Cut-offs | Ref. |
|---|---|---|---|---|---|---|---|---|
| p53 | Mouse MAb anti p53 | DO7 | Novocastra | 1:50 | Nuclear | % of positive cells | >10% (negative) 10-20 (low) >20% (High) | 13-16 |
| Bcl2 | Mouse MAb anti-Bcl2 | 124 | Dako-Cytomation | 1:100 | Cytoplasm | % of positive cells | >10% (positive | 13-16 |
| BRCA1 | BRCA1 | MS110 | Oncogen Research | 1:150 | Nuclear | % of positive cells | <25% (negative) | 13-16 |
| ATM | Rabbit MAb anti-ATM | Y170 | Abcam | 1:100 | Nuclear | % of positive cells | <25% (negative) ≥75% | 13-16 |
| p27 | anti-p27 | SX53G8 | Dako-Cytomation | 1:50 | Nuclear | % of positive cells | ≥10% (positive) | 13-16 |

SUPPLEMENTARY TABLE (S2)-continued

Antigens, primary antibodies, clone, source, optimal dilution and scoring system used for each immunohistochemical marker

| Antigen | Antibody | Clone | Source | Dilution | Distribution | Scoring system | Cut-offs | Ref. |
|---|---|---|---|---|---|---|---|---|
| Vimentin | Mouse MAb anti-vimentin | Vim 3B4 | Dako-Cytomation | 1:250 | Cytoplasm | % of positive cells | ≥10% (positive) | 13-16 |
| Bax | Rabbit anti-Bax | Polyclonal | Abcam | 1:1000 | Cytoplasm | % positive cells | ≥10% (positive) | 13-16 |
| ER | Mouse MAb anti-ER-α | 1D5 | Dako-Cytomation | 1:200 | Nuclear | Allred score | ≥3 (positive) | 13-16 |
| PR | Mouse MAb anti-PR | PR | Dako-Cytomation | 1:150 | Nuclear | Allred score | ≥3 (positive) | 13-16 |
| EGFR | Mouse MAb anti-EGFR | 31G7 | 1:50 | Zymed | Membrane | 0-3 as HER2 | 0 or +1 (negative) +2 or +3 (positive) | 13-16 |
| CK14 | Mouse MAb anti-Ck14 | LL002 | Novocastra | 1:40 | Cytoplasm | % of positive cells | ≥10% (positive) | 13-16 |
| Ck5/6 | Mouse MAb anti-Ck5/6 | D5/161B4 | Chemicon | 1:60 | Cytoplasm | % of positive cells | ≥10% (positive) | 13-16 |
| Ck17 | Mouse MAb anti-Ck17 | E3 | Dako-Cytomation | 1:100 | Cytoplasm | % of positive cells | ≥10% (positive) | 13-16 |
| Ck18 | Mouse MAb anti-Ck18 | DC10 | Dako-Cytomation | 1:100 | Cytoplasm | % of positive cells | ≥10% (positive) | 13-16 |
| HER2 | Rabbit antihuman c-erbB2 | polyclonal | Dako-Cytomation | 1:100 | Membrane | Ascogiudline | | 17 |
| Ki67 | Mouse MAb anti-Ki-67 | MIB1 | Dako-Cytomation | 1:300 | Nuclear | % of positive cells | <10% (low) 10-30% (moderate) >30% (high) | 13-16 |
| TOP2A | Mouse MAb TOP2A | KiS1 | D Dako-Cytomation | 1:150 | Nuclear/cytoplasm | % of positive cells | >25% (positive) | 13-16 |
| p21 | Mouse MAb anti-p21 | EA10 | Abcam | 1:25 | Nuclear | % of positive cells | ≥10% (positive) | 13-16 |

All sections were pre-treated with microwave antigen retrieval using 0.1% citrate buffer (pH 6) except for HER2 (no pre-treatment) and EGFR (pre-treated with protease for 10 minutes).

MDM2: murine double minute 2; MDM4: murine double minute 4; ATM: ataxia telangiectasia mutated; BRCA1: BC 1, ER: oestrogen receptor; PR: progesterone receptor; CK: cytokeratin; EGFR: epidermal growth factor; TOP2A: Topoisomerase II alpha; MAb: Monoclonal antibody.

TABLE (3)

Clinico-pathological characteristics of HAGE protein expression in primary operable Triple negative breast cancer (n = 520)

| | HAGE protein expression | | |
|---|---|---|---|
| Variables | Negative (n = 443) | Positive (n = 77) | p value |
| Bcl2 | | | 0.001* |
| Negative | 266 (66.8) | 61 (85.9) | |
| Positive | 132 (33.2) | 10 (14.1) | |
| BAX | | | 0.01* |
| Negative | 228 (79.7) | 44 (59.5) | |
| Positive | 58 (20.3) | 30 (40.5) | |
| FEN1 (Cytoplasmic) | | | 0.00008* |
| Negative | 252 (79.5) | 36 (56.3) | |
| Positive | 65 (20.5) | 28 (43.8) | |
| p21 | | | 0.009* |
| Negative | 286 (80.1) | 39 (65.0) | |
| positive | 71 (19.9) | 21 (35.0) | |
| Androgen receptor | | | 0.008* |
| Negative | 238 (83.7) | 54 (65.9) | |
| Positive | 66 (16.3) | 28 (34.1) | |
| Menopausal status | | | 0.010* |
| Pre | 197 (48.13) | 23 (32.4) | |
| Post | 206 (51.1) | 48 (67.6) | |
| Tumour type | | | 0.001* |
| IDC-NST | 348 (86.1) | 59 (84.3) | |
| Medullary/Atypical | 23 (5.7) | 3 (4.3) | |
| Tubular Carcinoma | 3 (0.7) | 5 (7.1) | |
| Invasive lobular carcinoma | 17 (4.2) | 0 (0) | |
| Others | 13 (3.2) | 3 (4.3) | |
| Lymph node stage | | | 0.090 |

TABLE (3)-continued

Clinico-pathological characteristics of HAGE protein expression in primary operable Triple negative breast cancer (n = 520)

| | HAGE protein expression | | |
|---|---|---|---|
| Variables | Negative (n = 443) | Positive (n = 77) | p value |
| Negative | 288 (65.2) | 47 (61.0) | |
| Positive (1-3 nodes) | 115 (26.0) | 17 (22.1) | |
| Positive (>3 nodes) | 39 (8.8) | 13 (16.9) | |
| Tumour grade | | | 0.418 |
| G1 | 5 (1.1) | 0 (0.0) | |
| G2 | 32 (7.2) | 8 (11.5) | |
| G3 | 405 (92.0) | 69 (88.5) | |
| Mitotic index | | | 1.00 |
| M1 (low; mitoses <10) | 23 (4.9) | 4 (5.3) | |
| M2 (medium; mitoses 10-18) | 40 (9.1) | 7 (9.2) | |
| M3 (high; mitoses >18) | 376 (85.6) | 65 (85.5) | |
| Tumor size | | | 0.869 |
| T1 a + b (=<1.0) | 14 (5.5) | 3 (3.9) | |
| T1 c (>1.0-2.0) | 190 (43.7) | 37 (48.1) | |

TABLE (3)-continued

Clinico-pathological characteristics of HAGE protein expression in primary operable Triple negative breast cancer (n = 520)

| | HAGE protein expression | | |
|---|---|---|---|
| Variables | Negative (n = 443) | Positive (n = 77) | p value |
| No | 93 (24.2) | 15 (24.6) | |
| Yes | 291 (75.8) | 46 (75.4) | |
| Ki67 | | | 0.628 |
| Negative | 55 (13.9) | 9 (11.8) | |
| Positive | 340 (86.1) | 67 (88.2) | |
| P53 | | | 0.267 |
| Negative | 169 (42.7) | 33 (50.0) | |
| Positive | 227 (57.3) | 33 (50) | |
| E-cadherin | | | 0.111 |
| Negative | 123 (32.7) | 14 (22.6) | |
| Positive | 253 (67.3) | 48 (77.4) | |
| P-cadherin | | | 0.672 |
| Negative | 60 (16.5) | 8 (14.3) | |
| Positive | 303 (83.87) | 48 (85.7) | |
| ATM | | | 0.507 |
| Negative | 222 (65.3) | 34 (60.7) | |
| Positive | 118 (34.7) | 22 (39.3) | |
| BRCA1 | | | 0.218 |
| Negative | 225 (63.2) | 30 (54.5) | |
| Positive | 131 (36.8) | 250 (45.5) | |

TABLE 4

Multivariate analysis using Cox regression analysis confirms that HAGE protein expression, Bcl2 and lymph node stage are independent prognostic factors in Triple negative breast cancer.

| | Breast cancer specific Survival at 10 years | | Progression Free Survival at 10 years | |
|---|---|---|---|---|
| Clinico-pathological variables | HR (95% CI) | P value | HR (95% CI) | P value |
| HAGE expression | | 0.00007* | | 0.002* |
| Low | 1 | | 1 | |
| High | 2.1 (1.5-3.1) | | 1.8 (1.2-2.5) | |
| Bcl2 expression | | 0.01* | | 0.02* |
| High | 1 | | 1 | |
| Low | 1.7 (1.1-2.6) | | 1.5 (1.1-2.2) | |
| Lymph node stage | | $6.7 \times 10^{-12}$* | | $1.2 \times 10^{-10}$* |
| Negative | 1 | | 1 | |
| Positive (1-3 nodes) | 1.5 (1.0-2.2) | | 1.3 (0.9-1.8) | |
| Positive (>3 nodes) | 4.5 (3.0-6.8) | | 3.8 (2.6-5.5) | |
| Tumour grade | | 0.469 | | 0.770 |
| Grade1 (low) | 1 | | 1 | |
| Grade 2 intermediate) | 0.5 (0.1-4.1) | | 0.8 (0.1-6.2) | |
| Grade 3 (high) | 0.8 (0.1-5.4) | | 1.0 (0.1-7.2) | |
| Tumour size (continuous) | 1.0 (1.0-1.1) | 0.428 | 1.0 (1.0-1.1) | 0.661 |
| Chemotherapy | | 0.007* | | 0.03* |
| No | 1 | | 1 | |
| Yes | 0.6 (0.5-0.9) | | 0.7 (0.5-1.0) | |
| Menopausal status | | 0.023* | | 0.092 |
| Pre | 1 | | 1 | |
| Post | 1.5 (1.1-2.1) | | 1.3 (1.0-1.7) | |

*Statistically significant

TABLE (3)-continued

Clinico-pathological characteristics of HAGE protein expression in primary operable Triple negative breast cancer (n = 520)

| | HAGE protein expression | | |
|---|---|---|---|
| Variables | Negative (n = 443) | Positive (n = 77) | p value |
| T2 (>2.0-5.0) | 202 (46.4) | 34 (44.2) | |
| T3 (>5) | 19 (4.4) | 3 (3.9) | |
| Basal like phenotype | | | 0.950 |

TABLE (5)

Pathological complete response (pCR) of HAGE expression for anthracycline combination chemotherapy of primary locally advanced triple negative breast cancers: Univariate analysis

| | Pathological Response | | |
|---|---|---|---|
| HAGE Expression | Residual Disease | pCR | p |
| Low (−) | 43 (91.9%) | 4 (8.5%) | 0.009 |
| High (+) | 22 (68.8%) | 10 (31.3%) | |

TABLE (6)

Pathological complete response (pCR) of HAGE expression for anthracycline combination chemotherapy of primary locally advanced triple negative breast cancers: Multivariate regression

| Variables | Expression | OR | 95% CI | p |
|---|---|---|---|---|
| HAGE | Low | 1 | | 0.027* |
| | High | 2.28 | 1.1-4.7 | |
| Age at diagnosis | continuous | 0.98 | 0.92-1.04 | 0.467 |
| Maximum tumour diameter | continuous | 1.00 | 0.97-1.03 | 0.952 |
| Tumour grade | | | 0.05-0.98 | 0.048 |
| | G1-2 | 1 | | |
| | G3 | 0.22 | | |
| Tumour T stage | | | | 0.534 |
| | T1-2 | 1 | | |
| | T3-4 | 1.36 | 0.51-3.62 | |

The invention claimed is:

1. A method of screening for and treating aggressive breast cancer in a subject comprising
   a) obtaining a sample of breast tumour tissue from a subject;
   b) detecting whether the sample is HAGE+ wherein helicase antigen HAGE+ is defined as the presence of cytoplasmic and/or nuclear staining with an anti-HAGE antibody in more than 10% of malignant cells;
   c) diagnosing the subject as having an aggressive breast cancer or having an increased probability that the breast cancer is aggressive when the sample is HAGE+; and
   d) administering an effective amount of chemotherapy to a subject diagnosed as having an aggressive breast cancer or having an increased probability that the breast cancer is aggressive.

2. The method according to claim 1, wherein the tumour is also tested for the level of expression of one or more of an ER (estrogen receptor), a progesterone receptor (PR) and/or human epidermal growth factor 2 (HER2).

3. The method according to claim 2, wherein the amount of ER and/or PR and/or HER2 is detected using an anti- ER or a PR or a HER2 specific antibody or fragment thereof.

4. The method according to claim 1 wherein said chemotherapy is anthracycline chemotherapy (ACT) or adjuvant chemotherapy.

5. The method according to a claim 4 wherein the subject is HAGE+ ER− or HAGE+ ER− PR− HER2−.

6. The method according to claim 4, wherein the adjuvant chemotherapy comprises CMF (cyclophosphamide, methotrexate, 5-fluorouracil) or adjuvant anthracycline.

\* \* \* \* \*

UNITED STATES PATENT AND TRADEMARK OFFICE
CERTIFICATE OF CORRECTION

PATENT NO. : 9,791,448 B2
APPLICATION NO. : 14/389108
DATED : October 17, 2017
INVENTOR(S) : Adam Linley et al.

Page 1 of 1

It is certified that error appears in the above-identified patent and that said Letters Patent is hereby corrected as shown below:

In Column 25, Claim 1, Line 24, please replace "sample is HAGE+ wherein helicase antigen HAGE+ is" with -- sample is helicase antigen (HAGE)+ wherein HAGE+ is --

Signed and Sealed this
Thirteenth Day of February, 2018

Andrei Iancu
*Director of the United States Patent and Trademark Office*